United States Patent [19]

Sano et al.

[11] 4,362,609
[45] Dec. 7, 1982

[54] OXYGEN CONCENTRATION SENSOR

[75] Inventors: Hiromi Sano, Nagoya; Masatoshi Suzuki; Masahiro Hamaya, both of Anjo; Masami Ouki, Nagoya, all of Japan

[73] Assignee: Nippondenso Co., Ltd., Kariya, Japan

[21] Appl. No.: 246,435

[22] Filed: Mar. 23, 1981

[30] Foreign Application Priority Data

May 29, 1980 [JP] Japan .................................. 55-72282

[51] Int. Cl.$^3$ ............................................. G01N 27/58
[52] U.S. Cl. ................................................. 204/195 S
[58] Field of Search ............................ 204/195 S, 1 S

[56] References Cited

U.S. PATENT DOCUMENTS 4,057,477 11/1977 Weyl et al. .
4,123,131 10/1978 Pearce et al. ................. 204/195 S X
4,127,464 11/1978 Ichikawa et al. .
4,141,813 2/1979 Kita et al. .
4,187,163 2/1980 Steinke et al. .................... 204/195 S Primary Examiner—G. L. Kaplan
Attorney, Agent, or Firm—Cushman, Darby & Cushman

[57] ABSTRACT

An oxygen concentration sensor including a solid electrolyte member having two portions, one portion being exposed to a gas of interest and the other portion being exposed to the atmosphere, an inner cover formed with a first space communicating portion arranged to communicate with the other portion of the solid electrolyte member, and a water-proof cover enclosing the inner cover to define a ventilating passage between the inner cover and the water-proof cover and formed with a second space communicating portion maintaining the first space communicating portion of the inner cover in communication with the atmosphere through the ventilating passage. The second space communicating portion of the water-proof cover is axially spaced apart from the first space communicating portion of the inner cover by a predetermined distance. Also included is structure to prohibit the flow of water through said ventilating passage. The second space communicating portion is separated from this structure.

9 Claims, 6 Drawing Figures

OXYGEN CONCENTRATION SENSOR

BACKGROUND OF THE INVENTION

This invention relates to an oxygen concentration sensor suitable for use in sensing the concentration of oxygen in exhaust emissions of an internal combustion engine of an automotive vehicle, for example.

Oxygen concentration sensors of the prior art disclosed in U.S. Pat. Nos. 4,057,477, 4,127,464 and 4,141,813 are all constructed for mounting in an exhaust pipe of an automotive vehicle and are often splashed with water when the vehicle travels in rainy weather or is washed. If the water seeps through the cover and reaches the interior of the solid electrolyte member when its temperature is high, the solid electrolyte member is suddenly cooled. This may crack or rupture the solid electrolyte member, making it impossible for the member to generate an electromotive force.

SUMMARY OF THE INVENTION

This invention has as its object the provision of an oxygen concentration sensor of improved construction capable of obviating the aforesaid disadvantage of the prior art.

The outstanding characteristic of the invention is that there is provided, in an oxygen concentration sensor, means for preventing water scattered thereon from seeping therethrough and reaching the interior of the solid electrolyte member, thereby enabling the prevention of damage to the solid electrolyte member that might otherwise be caused by the water.

DESCRIPTION OF THE PREFERRED EMBODIMENTS

Figure 1:
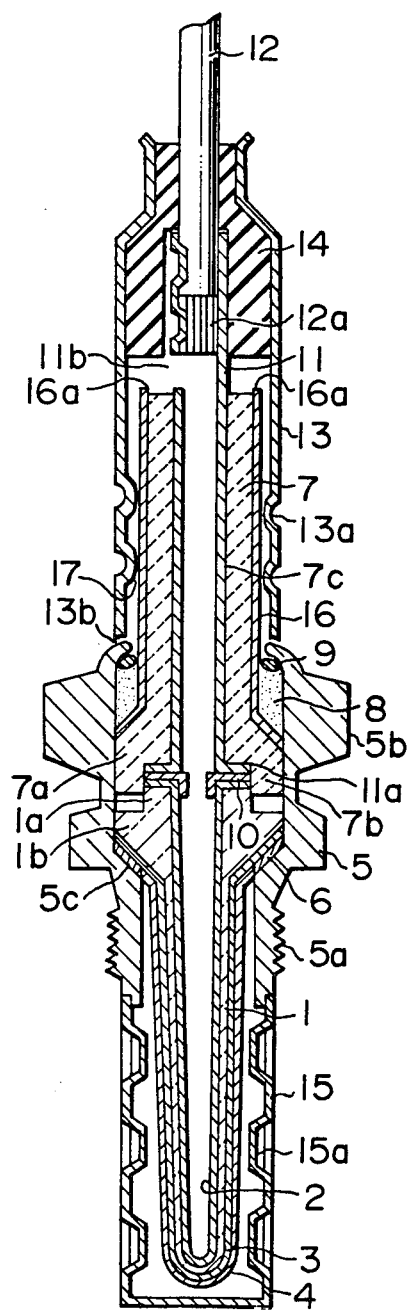
FIG. 1 is a sectional front view of the oxygen concentration sensor comprising one embodiment of the invention.

The invention will now be described in some detail by referring to the preferred embodiments thereof shown in the drawings. Referring to FIG. 1, a solid electrolyte member 1 for sensing the concentration of oxygen is formed of an oxygen ion conductive metal oxide which consists essentially of 95 mol% of zirconium oxide and 5 mol% of yttrium oxide solid-soluted therein, which member is substantially in the form of a tube closed at one end and open at the other end. The solid electrolyte member 1 is formed at its open end portion with a projection $1a$ surrounding the central opening thereof and an enlarged annular portion $1b$. The solid electrolyte member 1 has on its inner and outer wall surfaces first and second electrodes 2 and 3 respectively of platinum or one of platinum group metals having a catalyst action and formed by chemical plating, vaporization deposition in vacuum, baking of paste or chemical plating followed by electric plating.

The first electrode 2 extends to the top of the projection $1a$ of the solid electrolyte member 1, and the second electrode 3 extends from the closed end of the solid electrolyte member 1 to a conical portion at the lower end of the enlarged annular portion $1b$. The second electrode 3 is formed on its surface with a porous coat 4 of a heat resisting material, such as alumina or magnesia-alumina spinel, having a thickness of 50–150$\mu$.

The numeral 5 designates a cylindrical housing formed of heat resisting metal, such as stainless steel, having a threaded portion $5a$ and a hexagonal clamping nut portion $5b$ for securing the sensor to an exhaust pipe of an automotive vehicle, for example. The enlarged annular portion $1b$ of the solid electrolyte member 1 is supported on a tapering seat $5c$ on the inner surface of the housing 5 through a packing 6 of heat resisting metal, such as copper or nickel. The second electrode 3 of the solid electrolyte member 1 is electrically connected to the housing 5 through the packing 6 of a thickness of 0.5–1 mm.

The numeral 7 designates a tubular insulator formed of alumina porcelain having at one end an enlarged annular portion $7a$ formed at its forward end with a recess $7b$ positioned against the projection $1a$ of the solid electrolyte member 1. Inserted in an axial bore $7c$ formed in the center of the insulator 7 is a hollow pipe 11 formed of metal, such as stainless steel, which has a flange $11a$ resting on the top of the projection $1a$ of the solid electrolyte member 1 through a ring packing 10 formed of copper. By this arrangement, the solid electrolyte member 1 and insulator 7 have their ends positioned against each other with the inside of the recess $7b$ of the insulator 7 being arranged on the top of the projection $1a$ of the solid electrolyte member 1.

A cylindrical cover 16 formed of metal, such as stainless steel, is fitted over the outer periphery of the insulator 7 and formed with a space communicating portion $16a$ at its forward end. Filled between the cover 16 and the open end of the housing 5 is talc powder 8 on which is mounted a metal ring 9 which is caulked and directed radially to press the insulator 7 and solid electrolyte member 1 downwardly of the housing 5. The result of this is that a tapering surface of the enlarged annular portion $1b$ of the solid electrolyte member 1 is pressed against the packing 6 for the housing 5 and the flange $11a$ of the pipe 11 is pressed against the packing 10 for the solid electrolyte member 1, to secure the solid electrolyte member 1 and insulator 7 in place against movement within the housing 5.

The numeral 12 designates a lead having core wires $12a$ connected to the pipe 11 which is caulked. The numeral 13 designates a water-proof cover of the tubular shape formed of heat resisting metal, such as stainless steel, which is formed with a plurality of dents $13a$ on its surface for positioning the cover 13 which is fitted over the outer periphery of the insulator 7 and caulked so that a silicone rubber member 14 of the cylindrical shape located between the cover 13, lead 12 and pipe 11 is secured to the cover 13. A small clearance is defined between the dents $13a$ of the cover 13 and the cylindrical cover 16, which clearance serves as a ventilating passage 17.

The water-proof cover 13 is partially in contact at its end portion with the caulked portion of the housing 5, and a small clearance of about 1 mm is defined between the portions of the cover 13 and housing in contact with each other and serves as a space communicating portion $13b$. Thus the interior of the solid electrolyte member 1 communicates with the atmosphere through the space communicating portion $13b$, ventilating passage 17, space communicating portion 16a of the cover 16 and an opening 11b of the pipe 11.

The numeral 15 designates a protective cover of 0.5 mm in thickness formed of stainless steel which is provided with a plurality of windows 15a for allowing the exhaust gases to flow therethrough into the interior of the cover 15. The protective cover 15 is joined by welding to the housing 5 and encloses the solid electrolyte member 1.

The sensor is mounted on the exhaust pipe of an automotive vehicle, for example, at the threaded portion 5a of the housing 5, so that the outer periphery of the closed portion of the solid electrolyte member 1 is exposed to the exhaust gases.

In the aforesaid construction, the oxygen ions migrating through the solid electrolyte member 1 depending on the difference in concentration between the residual oxygen in the exhaust gases and the oxygen in the atmosphere generate an electromotive force which is taken out from between the lead 12 and housing 5.

As described hereinabove, the oxygen concentration sensor is mounted on the exhaust pipe of an automotive vehicle, for example, so that water is splashed thereon when the vehicle travels in rainy weather or is washed. If the water seeps through the protective cover into the interior of the solid electrolyte member 1 of high temperature, the solid electrolyte member 1 is suddenly cooled. This may cause cracking in or rupture of the solid electrolyte member 1, thereby making it impossible for the member 1 to generate an electromotive force.

In the embodiment shown and described hereinabove, the water-proof cover 13 is located outside the cover 16 fitted over the insulator 7 with the ventilating passage 17 being formed between the covers 13 and 16, and the space communicating portions 16a and 13a of the covers 16 and 13 respectively are not radially positioned against each other but axially spaced apart from each other. By virtue of this arrangement, the water splashed on the sensor is prevented from flowing through the ventilating passage 17 into the interior of the solid electrolyte member 1, thereby enabling damage to be avoided that would otherwise be caused by water.

Figure 2:
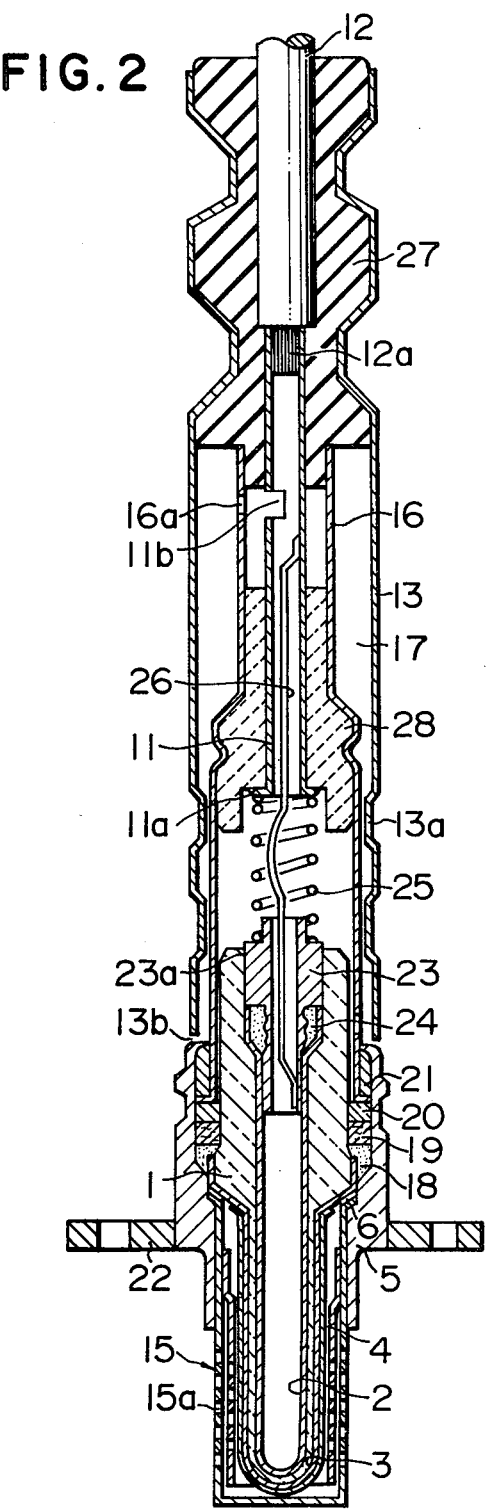
FIG. 2 is a sectional front view of the oxygen concentration sensor comprising another embodiment of the invention.

FIG. 2 shows another embodiment which is distinct in construction from the embodiment shown in FIG. 1 as follows. A conductive graphite powder layer 18, a ring-shaped asbestos layer 19 and a conductive metal ring 20 are located between the housing 5 and solid electrolyte member 1, and one end of the cover 16 formed of conductive and heat resisting metal, such as stainless steel, is arranged between the housing 5 and solid electrolyte member 1. A spacer ring 21 is disposed on one end of the cover 16, and the housing 5 is caulked at its upper end portion to secure the housing 5 to the solid electrolyte member 1 and at the same time to secure the one end of the cover 16 thereto. The housing 5 has a flange 22 secured thereto and attached to an exhaust pipe, not shown. The numeral 23 designates a stem formed with an axial bore 23a through its center, which is secured to the inner periphery of the solid electrolyte member 1 through a conductive graphite powder layer 24. The cover 16 has an insulating member 28 formed as of alumina secured to the other end thereof by caulking, and a hollow pipe 11 formed of conductive metal, such as stainless steel, is inserted in the central portion of the insulating member 28. A spring 25 is mounted between a flange 11a of the pipe 11 and a shoulder 23b formed in the stem 23, so that the stem 23 is forced against the solid electrolyte member 1 by the biasing force of the spring 25 to be firmly secured in place. The numeral 26 designates a stainless steel wire welded at one end to the wall of the axial bore 23a of the stem 23 and at the other end to the upper inner portion of the hollow pipe 11. An end portion of the hollow pipe 11 opposite the flange 11a has the lead 12 secured thereto by caulking. Thus the first electrode 2 of the solid electrolyte member 1 is electrically connected to the lead 12 via the graphite powder layer 24, stem 23, stainless steel wire 26 and pipe 11 with the spring 25 being mounted on the path, and the second electrode 3 thereof is electrically connected to the housing 5 via the conductive graphite powder layer 18 and conductive ring 20.

The water-proof cover 13 is secured at one end by caulking to a holding member 27 formed of silicone rubber for holding the lead 12 and in contact at the other end with a portion of the housing 5 which is caulked.

Figure 3:
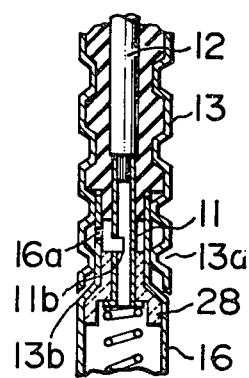
FIGS. 3 and 4 are sectional front views of other embodiments, showing the essential portions thereof.

FIG. 3 shows a modification of the embodiment shown in FIG. 2, in which the water-proof cover 13 has a reduced length and is prevented from coming into contact with the housing 5. The protective cover 13 contacts the cover 16 in the vicinity of the insulating member 28, and the dents 13a formed on the surface of the cover 13 are located in the vicinity of the insulating member 28.

Figure 4:
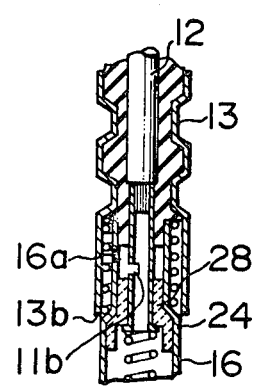

FIG. 4 shows another modification of the embodiment shown in FIG. 2, in which the water-proof cover 13 has a reduced length and the inner cover 16 has a metal wire 28 of about 0.5 mm in diameter wound spirally on its outer periphery with convolutions spaced apart from one another by about 1 mm so that the water-proof cover 13 is fitted over the spiral convolutions of metal wire 28 on the inner cover 16. In this modification, the interior of the solid electrolyte member 1 is maintained in communication with the atmosphere through the small gaps between the convolutions of metal wire 28 but in its construction water is hard to seep into the solid electrolyte member 1.

Figure 5:
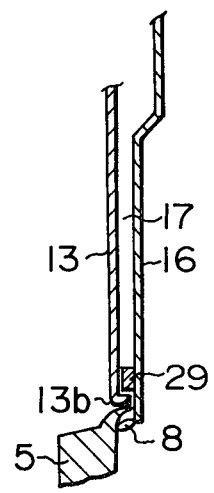
FIGS. 5 and 6 are sectional front views of still other embodiments, showing the essential portions thereof.

FIG. 5 shows a modification of the embodiment shown in FIG. 1, in which an annular plate 29 formed of metal is joined by welding to the cover 16 and the water-proof cover 13 has its end portion bent in a manner to surround the annular plate 29 with a small clearance therebetween. Also in the construction of this modification, water is hard to seep into the solid electrolyte member 1.

Figure 6:
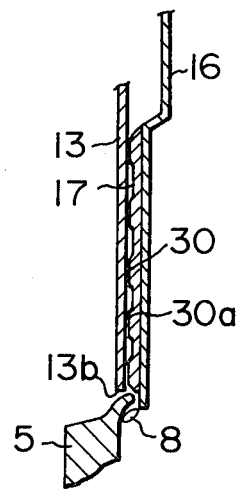

FIG. 6 shows another modification of the embodiment shown in FIG. 1, in which a cylindrical member 30 formed of silicone rubber is inserted in the cover 16 and has a corrugation 30a formed on its outer periphery. In this construction, the corrugation 30a is partly in contact with the inner surface of the water-proof cover 13 and prevents water from being introduced into the interior of the solid electrolyte member 1. The corrugation 30a has partly a gap between its elevated portion and the water-proof cover 13 which allows air to flow therethrough from the atmosphere.

The water-proof cover and inner cover 16 may, of course, be shaped such that the ventilating passage 17 therebetween is tortuous.

From the foregoing description, it will be appreciated that the present invention renders an oxygen concentration sensor water-proof by a simple construction.

What is claimed is:

1. An oxygen concentration sensor comprising:
   a solid electrolyte member including two portions, one portion being exposed to a gas of interest and the other portion being exposed to the atmosphere;
   an inner cover member formed with a first space communicating portion arranged to communicate with said other portion of said solid electrolyte member;
   a water-proof cover member enclosing said inner cover member and defining with said inner cover member a ventilating passage, said water-proof cover member being formed with a second space communicating portion for maintaining the first space communicating portion of said inner cover member in communication with the atmosphere through said ventilating passage, said second space communicating portion of said water-proof cover member being axially spaced apart from said first space communicating portion of said inner cover member; and
   means, disposed in said ventilating passage between said first and second space communicating portions and spaced axially from said first space communicating portion, for impeding the flow of water through said ventilating passage.

2. An oxygen concentration sensor as claimed in claim 1, wherein said impeding means includes a metal wire wound about the outer periphery of said inner cover member and positioned in said ventilating passage, so that the atmosphere can be maintained in communication with said other portion of said solid electrolyte member through a small clearance defined between turns of said metal wire.

3. An oxygen concentration sensor comprising:
   a solid electrolyte member including two portions, one portion being exposed to a gas of interest and the other portion being exposed to the atmosphere;
   an inner cover member formed with a first space communicating portion arranged to communicate with said other portion of said solid electrolyte member;
   a water-proof cover member enclosing said inner cover member and defining with said inner cover member a ventilating passage, said water-proof cover member being formed with a second space communicating portion maintaining said first space communicating portion of said inner cover member in communication with the atmosphere through said ventilating passage, said second space communicating portion of said water-proof cover member being axially spaced apart from said first space communicating portion of said inner cover member;
   a housing formed of metal caulked at one end portion for securing said inner cover member thereto and supporting said solid electrolyte member, said second space communicating portion of said water-proof cover member being defined by a clearance partially defined between said caulked one end portion of said housing and an end portion of said water-proof cover member; and
   means, disposed in said ventilating passage between said first and second space communicating portions and spaced axially from said first space communicating portion, for impeding the flow of water through said ventilating passage.

4. An oxygen concentration sensor as claimed in claim 1 or 3, wherein said impeding means includes a plurality of dents on a surface of said water-proof cover member for positioning said water-proof cover member in a spaced relationship from said inner cover member.

5. An oxygen concentration sensor as claimed in claim 1 or 3, wherein said second space communicating portion of said water-proof cover member comprises a clearance partially defined between one end of said water-proof cover member and a portion of the outer surface of said inner cover member close to said one end of said water-proof cover member.

6. An oxygen concentration sensor as claimed in claim 1 or 3, wherein said impeding means includes a ring of metal secured to the outer periphery of said inner cover member so that a clearance is defined between said ring and said water-proof cover member.

7. An oxygen concentration sensor as claimed in claim 1 or 3, wherein said impeding means includes a ring enclosed by one end portion of said water-proof cover member, said cover member being bent in a manner to define a clearance between said one end portion and said ring.

8. An oxygen concentration sensor as claimed in claim 1 or 3, wherein said impeding means includes a cylindrical member fitted over the outer periphery of said inner cover member, said cylindrical member having a corrugated outer periphery, to define a clearance between said corrugated outer periphery and said water-proof cover member.

9. An oxygen concentration sensor as claimed in claim 8, wherein said cylindrical member is formed of silicone rubber.

* * * * *